United States Patent
Faid et al.

(10) Patent No.: US 7,459,316 B2
(45) Date of Patent: Dec. 2, 2008

(54) MOLECULARLY-IMPRINTED CHEMICAL DETECTION DEVICE AND METHOD

(75) Inventors: Karim Faid, Nepean (CA); Christophe Py, Ottawa (CA); Farid Bensebaa, Gatineau (CA)

(73) Assignee: National Research Council of Canada, Ottawa, Ontario (CA)

( * ) Notice: Subject to any disclaimer, the term of this patent is extended or adjusted under 35 U.S.C. 154(b) by 675 days.

(21) Appl. No.: 10/614,158

(22) Filed: Jul. 8, 2003

(65) Prior Publication Data
US 2008/0268550 A1    Oct. 30, 2008

Related U.S. Application Data

(60) Provisional application No. 60/449,447, filed on Feb. 24, 2003.

(51) Int. Cl.
*G01N 33/543* (2006.01)
(52) U.S. Cl. .......................................... 436/518; 435/4
(58) Field of Classification Search .................... 435/4; 436/518
See application file for complete search history.

(56) References Cited

U.S. PATENT DOCUMENTS

| | | | |
|---|---|---|---|
| 5,110,833 A | 5/1992 | Mosbach | |
| 5,630,978 A | 5/1997 | Domb | |
| 6,096,386 A | 8/2000 | Biebuyek et al. | |
| 6,127,154 A | 10/2000 | Mosbach et al. | |
| 6,251,280 B1 * | 6/2001 | Dai et al. | 210/656 |
| 6,255,461 B1 | 7/2001 | Mosbach et al. | |
| 6,310,110 B1 | 10/2001 | Markowitz et al. | |
| 6,489,418 B1 | 12/2002 | Mosbach | |
| 7,020,355 B2 * | 3/2006 | Lahann et al. | 385/16 |
| 2002/0022275 A1 | 2/2002 | Furste et al. | |
| 2002/0037593 A1 | 3/2002 | Craighead et al. | |
| 2003/0027936 A1 | 2/2003 | Murray et al. | |
| 2004/0157209 A1 * | 8/2004 | Yilmaz et al. | 435/5 |

FOREIGN PATENT DOCUMENTS

| | | |
|---|---|---|
| WO | WO 01/88960 | 11/2001 |
| WO | WO 01/90228 | 11/2001 |

OTHER PUBLICATIONS

Whitesides et al., Annu. Rev. Biomed. Eng. 2001. 3:335-73.*
Bolshakova et al., Ultramicroscopy, vol. 86, Issues 1-2 , Jan. 2001, pp. 121-128.*
C. Sulitzky et al.: "Grafting of molecularly-imprinted polymer films on silica supports contating surface-bound free radical initiators." Macromolecules 2001.
S. Piletsky et al.: "Molecular imprinting: at the edge of the third millennium." Trends in Biotechnology, vol. 19, No. 1, Jan. 2001, pp. 9-12.

(Continued)

*Primary Examiner*—Jill Warden
*Assistant Examiner*—Natalia Levkovich
(74) *Attorney, Agent, or Firm*—J. David Barrans; Borden Ladner Gervais LLP

(57) ABSTRACT

A novel method of molecular imprinting is described. Using a modified soft lithography technique, a molecularly-imprinted chemical detection device comprising at least one molecularly-imprinted polymer capable of detecting at least one chemical target is produced. The device can be used in the field for in situ detection and quantification of chemical targets using standard surface analytical techniques.

18 Claims, 5 Drawing Sheets

OTHER PUBLICATIONS

A. Friggeri et al.: "From solutions to surfaces: a novel molecular imprinting method based on the conformational changes of boronic-acid-appended poly(L-lysine)." Angew. Chem. Int. Ed., vol. 40, No. 24, 2001, pp. 4729-4731.

T. Miyahara et al.: "Two-dimensional molecular imprinting: binding of sugars to boronic acid functionalized, polymerized Langmuir-Blodgett films." Chemistry Letters, 2000, pp. 1356-1357.

E. Yilmaz et al.: "The use of immobilized templates—A new approach in molecular imprinting." Angew. Chem. Int. Ed., vol. 39, No. 12, 2000, pp. 2115-2118.

H. Shi et al.: "Template-imprinted nanostructured surfaces for protein recognition." Nature, vol. 398, Apr. 1999, pp. 593-597.

M. Yan et al.: "Fabrication of molecularly imprinted polymer microstructures." Analytica Chimica Acta, vol. 435, 2001, pp. 163-167.

A. Jenkins et al.: "Polymer-based lanthanide luminescent sensor for detection of the hydrolysis product of the nerve agent soman in water." Anal. Chem., vol. 71, 1999, pp. 373-378.

K. Mosbach: "Toward the next generation of molecular imprinting with emphasis on the formation, by direct molding, of compounds with biological activity (biomimetics)." Analytica Chimica Acta, vol. 435, 2001, pp. 3-8.

"UCSD Chemists Develop Portable Nerve Gas Sensor", Science Daily, Aug. 22, 2000.

O. Ramstrom et al.: "Artificial antibodies to corticosteroids prepared by molecular imprinting", Chem. Biol., vol. 3, No. 6, Jun. 1996, pp. 471-477.

Shi Huaiqiu et al., "Template-imprinted nanostructured surfaces for protein recognition", *Nature*, vol. 398, No. 6728, Apr. 15, 1999, pp. 593-597.

Yan et al., "Fabrication of molecularly imprinted polymer microstructures", *Analytica Chimica Acta*, vol. 435, No. 1, May 17, 2001, pp. 163-167, XP002282361.

Uezu et al., "Molecular Recognition Using Surface Template Polymerization", *Chemtech*, Apr. 1999, pp. 12-18, XP002946323.

Hsia, et al., "Collapse of Stamps for Soft Lithography due to Interfacial Adhesion", Applied Physics Letters, Apr. 6, 2005, vol. 86, Issue 15, id. 154106 (3 pages).

* cited by examiner

MOLECULARLY-IMPRINTED CHEMICAL DETECTION DEVICE AND METHOD

CROSS-REFERENCE TO RELATED APPLICATIONS

This application claims the benefit of prior-filed U.S. provisional application Ser. No. 60/449,447, filed on Feb. 24, 2003.

FIELD OF THE INVENTION

The present invention relates generally to a method of molecular imprinting. More particularly, the present invention relates to a novel molecularly-imprinted chemical detection device comprising molecularly-imprinted polymers.

BACKGROUND OF THE INVENTION

Over the past few decades there has been considerable development of highly sensitive and specific detection devices, particularly in the fields of biochemistry and molecular biology. Development has revolved around the use of time-honoured biomolecules such as enzymes, antibodies, oligonucleotides and other protein or DNA/RNA based compounds, which inherently possess remarkable recognition characteristics in biological systems. Recently, attention has turned to in situ detection technology, such as enzyme linked immunosorbent assays (ELISA) and microarrays. Progress has been hampered, however, because of the relative instability of these biomolecules in conditions outside of their native milieu, thus resulting in situations where reliability is compromised. In abnormal temperature and pH environments, proteins often degrade, losing their tertiary/quaternary structures and their inherent functionality. Fragmentation of nucleic acid probes and targets is typical, leading to false positive results. While "DNA chips" and other comparable microarray devices have only recently begun to achieve commercial success, they have been plagued by a lack of coherent and flexible detection criteria. Protein-based detection technology is still in a troubled infancy, hampered by logistical problems with the stabilization of the protein target to the array surface. Methods for the detection of biochemicals often lack sufficient sensitivity and specificity to discriminate between similarly structured entities. Furthermore, the methods used tend to be bulky, expensive, laborious and often involve dangerous chemicals for analysis.

Thus, there was a need to develop artificial recognition elements which could simulate the sensitive and specific detection capabilities of biomolecules. This need led to the discovery of molecular imprinting. Standard molecular imprinting is a process by which guest molecules (functional monomers or polymers) are allowed to self-assemble around a molecular target, conforming its shape into a recognition element, in relation to stearic interactions at binding sites corresponding to functional groups in the target molecule. The recognition elements form a binding cavity which is cross-linked into a matrix. The target molecule is removed, leaving behind a molecularly-imprinted polymer (MIP) complementary in shape and functionality to the target molecule, which will rebind chemical targets identical to the original molecular target. The MIP functions like a lock that is only compatible with the correct key. Molecular imprinting has been used in column chromatography and silica gel applications (Sulitzky et al., Macromolecules 2001) and for the synthesis of polymeric materials that mimic biological receptors.

Molecular recognition between a chemical target and its corresponding MIP requires high order discrimination at the binding sites; this can happen only if the binding sites of the MIP and chemical target complement each other in size, shape, orientation, and chemical functionality. MIPs possess high affinity and selectivity (similar to natural receptors and antibodies), are uniquely stable as compared to natural biomolecules, are relatively simple to prepare, and easily adaptable to different applications (Piletsky et al., 2001).

Early work in molecular imprinting, particularly by Wolff et al., provided a guest molecule-molecular target interaction whereby aggregates in solution are maintained by reversible covalent bonds. Recent development by Mosbach and others has focussed on the "supra-molecular assembly" approach, whereby the pre-arrangement between the molecular target and the guest molecule is formed by non-covalent or metal co-ordination interactions.

The guest molecule-molecular target complex is then copolymerized with a cross-linker, leading to a highly cross-linked macroporous polymer with the imprint molecules in a sterically-fixed arrangement. This forms a highly-specific recognition element capable of recognizing a molecular target. The cross-linker forms an insoluble polymer with substantial rigidity. Since a very high degree of cross-linking (70-90%) is necessary for achieving specificity, only a limited number of cross-linkers have been utilized. Further, introducing external cross-linkers to the imprinting process can potentially hinder MIP formation if cross-linking at undesired locations within the MIP occurs. Several different cross-linkers have been tried with different degrees of success. Originally, isomers of divinylbenzene were used for cross-linking of styrene and other functional monomers into polystyrenes. Later, it was found that acrylic or methacrylic based systems could be prepared with much higher specificity. In addition to cross-linkers which are non-polar or weakly polar in nature, cross-linkers containing functional groups have been studied (Ramström, 1996).

Typically, binding cavities comprising the polymerized guest molecule have been cross-linked into three-dimensional "blocks" which recognize targets which become embedded within their structure. The block of polymer is then crushed, ground and filtered to produce appropriate particle sizes. The particles generated are irregular and some binding sites may be destroyed by the grinding process. The three-dimensional nature of these materials has an effect on the porosity of the matrix, meaning that adsorption and desorption kinetics play a major role in their effectiveness. Moreover, and because no direct analytical technique (such as surface plasmon resonance (SPR), cantilever or evanescent-based techniques) can probe the adsorption of the target molecules, multiple chemical steps, such as extraction, concentration, labelling etc., are required. This series of steps has hindered the use of MIPs outside of the lab setting. Such three-dimensional polymers have been described by Mosbach and in U.S. Pat. No. 6,310,110, issued to Markowitz et al.

Molecular imprinting had been typically carried with the molecular target as a free, unbound moiety in solution target free in solution. Because the molecular targets are not fixed to a solid surface, the quality of the MIPs can be compromised, resulting in binding sites which are heterogeneous in their orientation, shape and affinity for/accessibility to the target molecule. U.S. Pat. No. 5,630,978, issued to Domb, discloses an in vitro method for the preparation of mimics of drugs and other biologically active molecules.

Recent progress has been made in surface immobilization of the molecular target on a solid support. Friggeri et al.

(*Angew. Chem. Int. Ed.* 2001; 40(24):4729-4731) describe a novel, solution-to-surface imprinting method based on the different higher-order conformations adopted by boronic acid appended poly-L-lysine. A molecular imprinted surface using boronic acid for binding sugars has been described by Miyahara and Kurihara (Chemistry Letters 2000; 1356), and using theophylline on aminopropyl-derivatized silica gel has been described by Yilmaz et al. (Angew. Chem. Int. Ed. 2000; 39(12):2115-2118).

PCT application WO 01/90228 (Mosbach et al.) discloses a molecular imprinting technique using immobilized templates for imprinting. This process ensures that the imprinted polymers produce uniform and structurally well-defined binding sites. The binding sites are located at or close to the surface of the polymer. This method uses a less reliable three-dimensional MIP which must be degraded with harsh chemicals (such as hydrofluoric acid) and loaded into a chromatography column for detection of bound targets. Similar imprinting methods are described in U.S. Pat. No. 6,489,418 and U.S. Pat. No. 6,127,154, both also issued to Mosbach.

Shi et al. (Nature 1999; 398:593-7) describe a method for synthesizing molecular target-imprinted surfaces for protein recognition. The target protein used is adsorbed to a mica thin layer. The "cavity" is formed from a saccharide which coats the protein. A plasma film overlays the cavity and is attached to a solid support. Although the system shows differential recognition of similar elements through strict conformational structures, its use appears to be limited to biological-based target proteins (such as antibody IgG and albumin). A method for making imprinted protein recognition sites for use in synthetic enzyme and antibody applications is disclosed in U.S. Pat. No. 5,110,833, issued to Mosbach. PCT application WO 01/88960 (Polyani et al.) describes a process for forming an imprinted pattern of adsorbed molecules on a solid surface.

Soft lithography represents a new alternative for fabricating MIP microstructures on two-dimensional substrates, rather than in the traditional three-dimensional matrix. The original version of this technology employed an elastomeric stamp (or mold), typically made of poly(dimethylsiloxane) (PDMS), to pattern a wide variety of materials such as self-assembled monolayers (SAMs), organic polymers, colloids, inorganic solids, proteins, and cells. The stamp is then placed in contact with a solid substrate, such as a gold coated glass slide. Although standard soft lithography is a relatively simple technique which requires no special equipment and can routinely be performed in the typical laboratory, deformations and distortions can be readily introduced due to the flexibility of the elastomeric stamp leading to errors in the replicated pattern.

A technique for fabricating MIP microstructures on silicon wafers using soft lithography has been described by Yan and Kapua (*Anal. Chim. Acta* 2001; 435:163-67). A PDMS stamp is contacted with a wafer creating microchannel structures on its surface. Formation of the MIP is achieved by fluidic means whereby the functional monomers are injected into the microcapillaries. Once the stamp is removed, the micro-channels are imprinted with MIPs. This method relies on capillarity to fill the channels with the polymer and bind target molecules to the MIPs. The method is somewhat impractical, however, as the detection of bound targets requires the use of lab-based technology such as column chromatography, HPLC, or GC/MS.

Methods for synthesizing MIPs have usually been limited to one molecular target of interest. Because of this, the use of molecular imprinting technology in a wide assortment of applications has been restricted. This is particularly crucial for the detection of biochemical families which as an ensemble may be responsible for the accurate diagnosis of certain diseases, such as, for example, the levels of dopamine in Parkinson's Disease or in the monitoring of different troponin isoforms in myocardial infarction.

The detection of hazardous and potentially lethal chemicals has become increasingly essential with continued threats of bioterrorism and the presence of harmful pollutants in the atmosphere. Detection and quantification of these toxic compounds at very low levels are critical, and must be done quickly so that appropriate precautions can be taken and/or emergency treatment can be provided. Although a variety of physical, chemical and biological techniques have been investigated, few detectors are small and inexpensive enough to be used in situ, such as in military or environmental applications. In addition, methods for the unambiguous detection and quantification of specific gasses usually involves separate sampling and analysis steps using complex and expensive equipment such as gas chromatography/mass spectrometry and HPLC. Devices based on this technology are not portable and are expensive and/or require extensive analysis procedures making them undesirable for real-time field analysis. Testing can take up to 24 hours to perform and typically lack specificity and simplicity. Existing detection devices can yield high false positive rates, particularly in attempts to distinguish nerve gasses (such as sarin) from other organophosphorous compounds which can be found in pesticides and insecticides.

With the recent surge in interest and necessity for the detection of nerve gasses and other potentially lethal chemicals, attempts have been made to manufacture sensitive chemical detection devices. However, very few use direct quantification of toxin of interest. A silicon chip sensor, designed by Trogler and colleagues at the University of San Diego for the U.S. Army ($220^{th}$ meeting of the American Chemical Society, 2000), uses a molecular catalyst to break the phosphorous-fluorine bond in "G"-type nerve agents. The product of this reaction, hydrogen fluoride, is detected with a silicon interferometer. The device, therefore, uses an indirect method of nerve gas detection and quantification. Hazardous chemical sensors are described in US Application 2003/0027936 (Murray et al.) and by Jenkins et al. (Anal Chem. 1999; 71(2):373-8).

It is, therefore, desirable to provide a novel method of producing a molecularly-imprinted chemical detection device.

SUMMARY OF THE INVENTION

It is an object of the present invention to obviate or mitigate at least one disadvantage of previous molecular imprinting methods. Advantageously, certain embodiments of the invention can be produced quite readily and inexpensively in any typical laboratory setting.

According to the invention there is provided a method of producing a portable, molecularly-imprinted chemical detection device using a soft lithography printing technique modified from traditional solid support molecular imprinting methodologies.

It is a further object of the present invention to provide a molecularly-imprinted chemical detection device comprising a solid substrate and one or more molecularly-imprinted polymers on the surface of the solid substrate surface.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
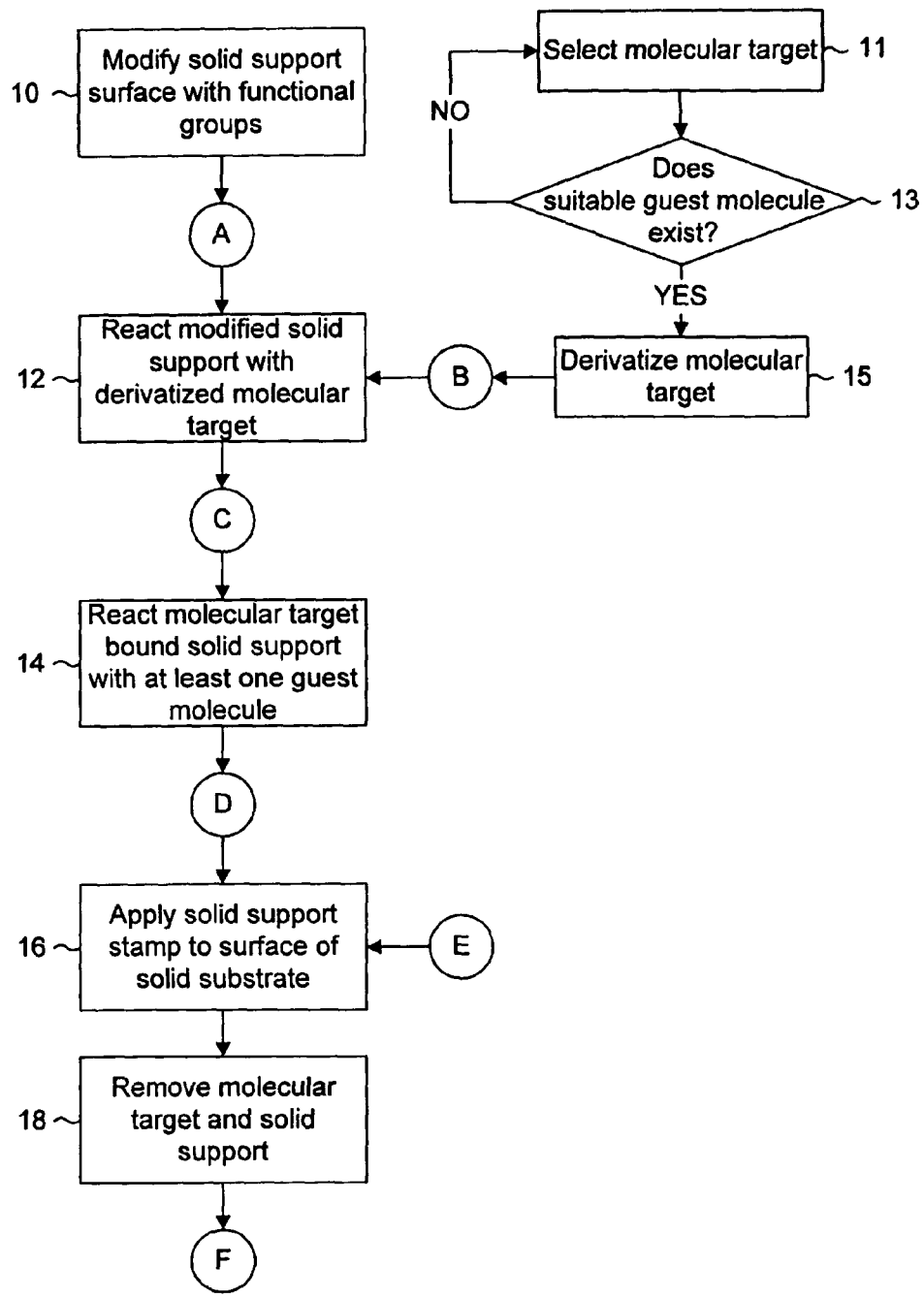
FIG. 1 is a flowchart illustrating the overall method of producing a molecularly-imprinted chemical detection device according to an embodiment of the present invention.

Generally, the present invention provides a novel method of producing a molecularly-imprinted chemical detection device. Specifically, the invention provides a method of producing a molecularly-imprinted chemical detection device comprising the steps of modifying the surface of a solid support through the attachment of functional groups, reacting the solid support with a derivatized molecular target to form a molecular target bound solid support, reacting the molecular target bound solid support with at least one guest molecule thus forming a solid support stamp having a binding cavity around the molecular target, applying the solid support stamp to a surface of a solid substrate to attach the binding cavity to the solid substrate, and removing the molecular target and solid support to produce a molecularly-imprinted polymer on the surface of the solid substrate.

In this specification, a "molecular target bound solid support" refers to any solid support with an attached derivatized molecular target. The solid support can be any solid surface, such as a silicon wafer. The support is modified, such as with amino-siloxane, such that functional groups are exposed to facilitate attachment to a derivatized molecular target. Any molecular target may be used so long as it is derivatized with a functional group that will bind to the functional group on the surface of the solid support.

In this specification, a "guest molecule" refers to a derivatized functional monomer or polymer capable of forming a binding cavity around the molecular target bound to the molecular target bound solid support. In one embodiment of the present invention, the guest molecules are at least two derivatized functional monomers which form recognition elements around the molecular target. These recognition elements are then polymerized to form a binding cavity around the molecular target. In one embodiment, the guest molecules are derivatized with thiol functional groups.

In one embodiment, computer-aided molecular modeling is used to identify binding sites on proposed molecular targets. This information is used to identify suitable guest molecules by modeling the interaction of the guest molecules with the molecular targets. Guest molecules are ranked according to their binding ability with the molecular targets. Once suitable guest molecules are determined, docking software programs can be used to rank the guest molecules by determining the most optimal binding free energies between molecular targets and the guest molecule.

In this specification, a "solid support stamp" refers to a molecular target bound solid support having a binding cavity around the molecular target. The solid support stamp is applied to a surface of a solid substrate to attach the binding cavity to the solid substrate. In this application, a "solid substrate" can be any solid material that is suitable for the detection techniques to be used. In one embodiment, a glass slide is used having an area of about 1 to 2 cm$^2$ and coated with gold for detection using a surface plasmon resonance. In another embodiment, the slide is coated with silicon dioxide for detection using an evanescent-based technique.

At least one binding cavity can be applied to the surface of the solid substrate by the solid support stamp. Removing the molecular target and solid support produces a molecularly-imprinted polymer (MIP) attached to the surface of the solid substrate. At least one MIP can be attached to the solid substrate. In one embodiment of the present invention, the MIPs are attached to the substrate via sulfide bonds created from the reaction of the solid substrate with thiol groups on the exterior surface of the binding cavity. According to the present invention, the surface-attachable thiol groups act as cross-linkers between the binding cavity and the solid substrate, reducing the need for external cross-linking agents and increasing the proportion of recognition elements in the system.

The MIPs can be arranged in any pattern on the surface of the solid substrate. In one embodiment, a plurality of MIPs are patterned on the surface of the solid substrate in a linear array format. In another embodiment, at least two different binding cavities are attached to the solid substrate producing at least two different molecularly-imprinted polymers segregated into separate areas.

The present invention further provides a molecularly-imprinted chemical detection device comprising a planar solid substrate and at least one molecularly-imprinted polymer imprinted on a surface of the planar solid substrate. The device can be synthesized according to the above method.

An advantage of the device of the present invention is that it is lightweight and can be palm-sized for convenient portability. The device can be used in the field outside of the laboratory setting.

The present application further provides a method of detecting a chemical target using a molecularly-imprinted chemical detection device comprising the steps of exposing the device to the chemical target and directly detecting the binding of the chemical target to at least one molecularly-imprinted polymer imprinted on a surface of the device. One advantage of this method is that the detection of bound chemical targets can be achieved through the use of existing direct analytical detection techniques, such as surface plasmon resonance, infra-red (IR) spectroscopy, raman spectroscopy, X-ray photoelectron spectroscopy (XPS), photonic detection, evanescent detection, cantilever detection and time-of-flight secondary ion mass spectroscopy. This method further provides the determining of a concentration of chemical targets bound to the at least one molecularly-imprinted polymer imprinted on a surface of the device.

One advantage of the detection and quantification methods of the present invention is that low level detection and quantification of chemicals can be done in situ, outside of the laboratory setting. In one embodiment, nerve gas is detected and quantified in military applications. In another embodiment, the method provides point-of-care monitoring of, for example, drug levels in patients receiving medical treatment or biochemicals in the diagnosis of diseases such as Parkinson's or Alzheimer's disease.

FIG. 1 is a flowchart illustrating the overall method of producing a molecularly-imprinted chemical detection device according to an embodiment of the present invention. A solid support surface is modified (10) with functional groups to produce a modified solid support (A). In one embodiment, the solid support can be modified with aminosilane such that the solid support is aminated. The modified solid support is reacted (12) with a derivatized molecular target to produce a molecular target-bound solid support (C). The molecular target-bound solid support is reacted (14) with at least one guest molecule (B). If a monomer guest molecule is added to the molecular target-bound solid support, the monomers form a recognition element around the molecular target on the surface of the molecular target-bound solid support. The recognition element is then polymerized, thus forming a binding cavity. If a polymer guest molecule is added to the molecular target-bound solid support then no polymerization step is required and a binding cavity is formed from the polymerized guest molecule. The molecular target-bound solid support with a binding cavity attached to it forms a solid support stamp (D). The solid support stamp is applied (16) to the surface of a solid substrate (E), which is typically a gold or silicon dioxide coated glass slide. The solid support and molecular target are then removed (18), leaving behind the binding cavity on the surface of the solid substrate. The binding cavity can attach to the solid substrate either through covalent or non-covalent interactions. Once attached, the binding cavity forms a molecularly-imprinted polymer. A molecularly-imprinted chemical detection device (F) comprises the solid substrate and the molecularly-imprinted polymer.

To obtain a derivatized molecular target (B), a molecular target is selected (11). Using computer-aided molecular modeling, one or more suitable guest molecules are identified by modeling the interaction of the guest molecules with the molecular target of interest (13). If no suitable guest molecule exists, an alternate molecular target is selected. If a suitable guest molecule exists, the molecular target is derivatized (15) to have a free functional group capable of binding to the modified solid support.

Figure 2:
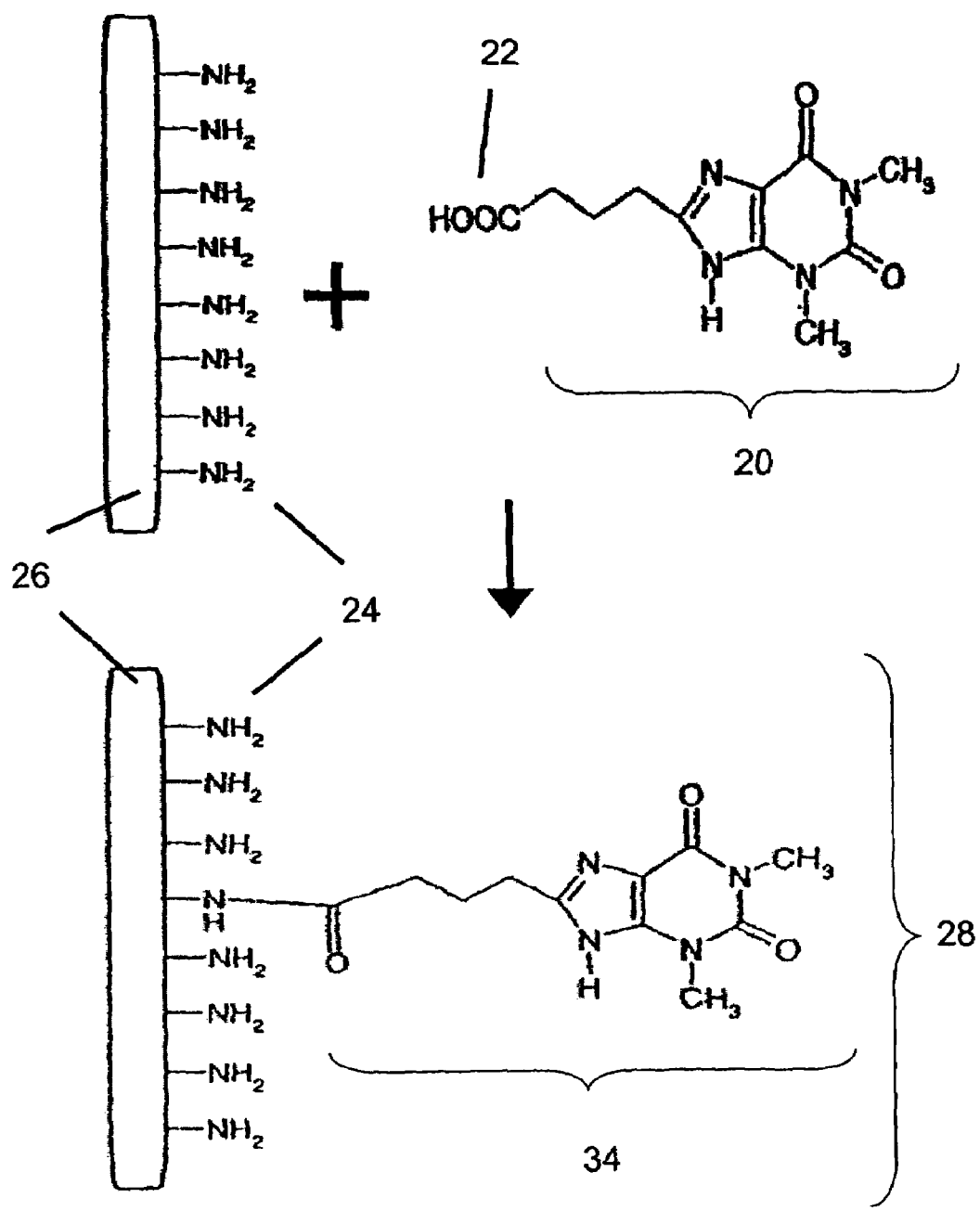
FIG. 2 provides an example of attachment of a carboxylic-derivatized theophylline molecular target to a modified solid support forming a molecular target bound solid support.

FIG. 2 illustrates an example of using carboxylic-derivatized theophylline as a molecular target attached to a modified aminated solid support. A molecule of carboxylic-derivatized theophylline 20 is reacted with a solid support 26 which has been modified with amino groups 24. Through the reaction of the carboxylic end group 22 with an amino group 24, the theophylline molecule is attached to the solid support. The molecular target 34 bound to the solid support 26 produces a molecular target-bound solid support 28.

By way of example, the substrate used in the modification of the solid support is $Si/SiO_2$ (300 nm thermal oxide on Si(100)). The $Si/SiO_2$ surface is cleaned and hydroxylated in piranha solution and is immersed in a 100 mM solution of aminopropylmethyldiethoxysilane (APMDES=$H_2N$—$(CH_2)_3$—Si—$(OC_2H_5)_2CH_3$) in ethanol. The reaction is carried out under inert atmosphere (argon purge). After an overnight reaction, the samples are thoroughly rinsed with ethanol and dried under a nitrogen stream. The modified substrates are characterized by ellipsometry and XPS. The attachment of the aminosilane is confirmed by ellipsometry which proves the existence of a silane with a thickness of approximately 7.1 Å, which is in good agreement with the expected thickness (7-10 Å) and can be considered as a monolayer. The variable angle XPS measurements prove the attachment of aminosilane on the substrate. Survey and high resolution spectra are acquired for Si, C, O and N. The existence of nitrogen as indicated by a N(1s) signal at 400.1 eV resulting from aliphatic free amine groups clearly proves the presence of the aminosilane layer on the $Si/SiO_2$ substrate. High resolution spectrum of N(1s) also shows a small contribution from a protonated amine group, at 402.1 eV. Silicon exhibits two types of signatures: Si—C and Si—O. A Si—C peak at 101.8 eV increases in intensity as the take-off angle is increased, which is a good indication that Si—C is really at the interface between $Si/SiO_2$ and the silane.

As an example of binding a molecular target to a modified solid support, the amine-modified surface of a solid support is used for the grafting of the carboxylic acid derivative of theophylline (8-carboxypropyltheophylline). Theophylline is added to a mixture of two anhydrous solvents—dimethylformamide and dichloromethane—under inert atmosphere (argon purge). Carbodiimide is also added to this solution and then the amine-modified surface is immersed in a vial. The argon purge is maintained for 20 minutes and then the sealed vial is left overnight. The sample is rinsed copiously with dichloromethane and dried under a stream of nitrogen. XPS confirms that the reaction took place: the N1s spectrum shows changes when compared to the N1s characteristic to the aminosilane surface, corresponding to the nitrogen in the amide bond and the nitrogen in the heterocycle of the theophylline. The C1s also changed significantly with respect to the C1s spectrum in the aminosilane substrate due to new C type groups. After reaction with theophylline, carbonyl groups occur from the amide bond and from the theophylline.

XPS measurements prove the composition of the theophylline monolayer obtained on the amino-terminated surface. The ratio between C/N, (Si—C)/N and C/(Si—C) signals are in very good agreement with the ratio of these atoms corresponding to the molecular formula of the 8-carboxypropyltheophylline linked through an amide bond to the aminosilane monolayer.

Ellipsometry measurements indicate a thickness of 20.83 Å for the theophylline attached trough an amide bond, which is typically in the right range for this type of monolayer, given that the thickness of the thermal oxide can vary on the same wafer.

The same chemistry can be applied to another carboxylic derivative of theophylline, 7-acetic acid. XPS measurements confirm that the reaction took place as expected, proving that the 7-acetic acid theophylline is binding to the amino-surface through an amide bond.

ATR-FTIR is useful and complementary to XPS in characterizing the surface of the solid support after the modification. This method requires an intimate contact between the surface to be analyzed and the ATR crystal. For this purpose, the same type of modification can be applied to PDMS (polydimethylsiloxane) surfaces. For PDMS, the solvents of choice are water or ethanol. In this example, ethanol was chosen. Hydroxylated PDMS surfaces are obtained by $O_2$ plasma treatment for 1 minute. All the subsequent reactions are performed in ethanol. Trifluoroacetic anhydride is used for the "quenching" of any $NH_2$— groups left un-reacted after the reaction with theophylline-7-acetic acid. ATR-IR spectra exhibit the characteristic signature of the amide group (1660 and 1550 $cm^{-1}$) and a peak at 1710 $cm^{-1}$ that corresponds to the carbonyl groups in the theophylline molecule. These data prove that the attachment of the theophylline is taking place on amino-modified PDMS surface. No peaks corresponding to the trifluoroacetic anhydride are observed.

This series of surfaces was reproduced on $Si/SiO_2$ and characterized also by contact angle, after every step of modification. The hydroxylated surface exhibits an angle of 28.7° that changes to 66.7° upon modification with aminosilane. The theophylline surface has an angle of 50.6° (more hydrophilic than the amino surface) and after trifluoroacetic anhydride step, there is no change (51.1°) in the contact angle. The characterization was completed by ATR-FTIR spectroscopy for the substrates after each step of modification. The substrates were PDMS surfaces. Spectra for PDMS_OH, PDMS_aminosilane, PDMS_theophylline, PDMS_theophylline/ trifluoroacetic anhydride surfaces are taken. The signatures for —OH, —NH$_2$, amide group for the binding of the carboxylic derivative of theophylline are observed for each surface. The last step, the reaction with the trifluoroacetic anhydride, does not exhibit any peak characteristic to this molecule. Measurements by contact angle confirm the values obtained on the same series of samples with the Si/SiO$_2$ as substrate.

The XPS measurements on this series are difficult because the samples degas for a very long time. The bands are broad because the charge neutralization was not effective. The N signal proves that the reaction with the theophylline takes place.

A complete series of surfaces are prepared on Si/SiO$_2$ for XPS measurements in order to verify that the reactions in ethanol present the same products as the ones in which a mixture of solvents were used. The C and N signals prove that the modification of the surface with theophylline takes place on the amino-substrate. The spectra registered after the reaction with the trifluoroacetic anhydride show no difference when compared with the one characteristic to the theophylline-bound surface.

Theophylline-modified surfaces produced according to the present invention have been found to be stable at least after 13 days storage in ethanol.

Figure 3:
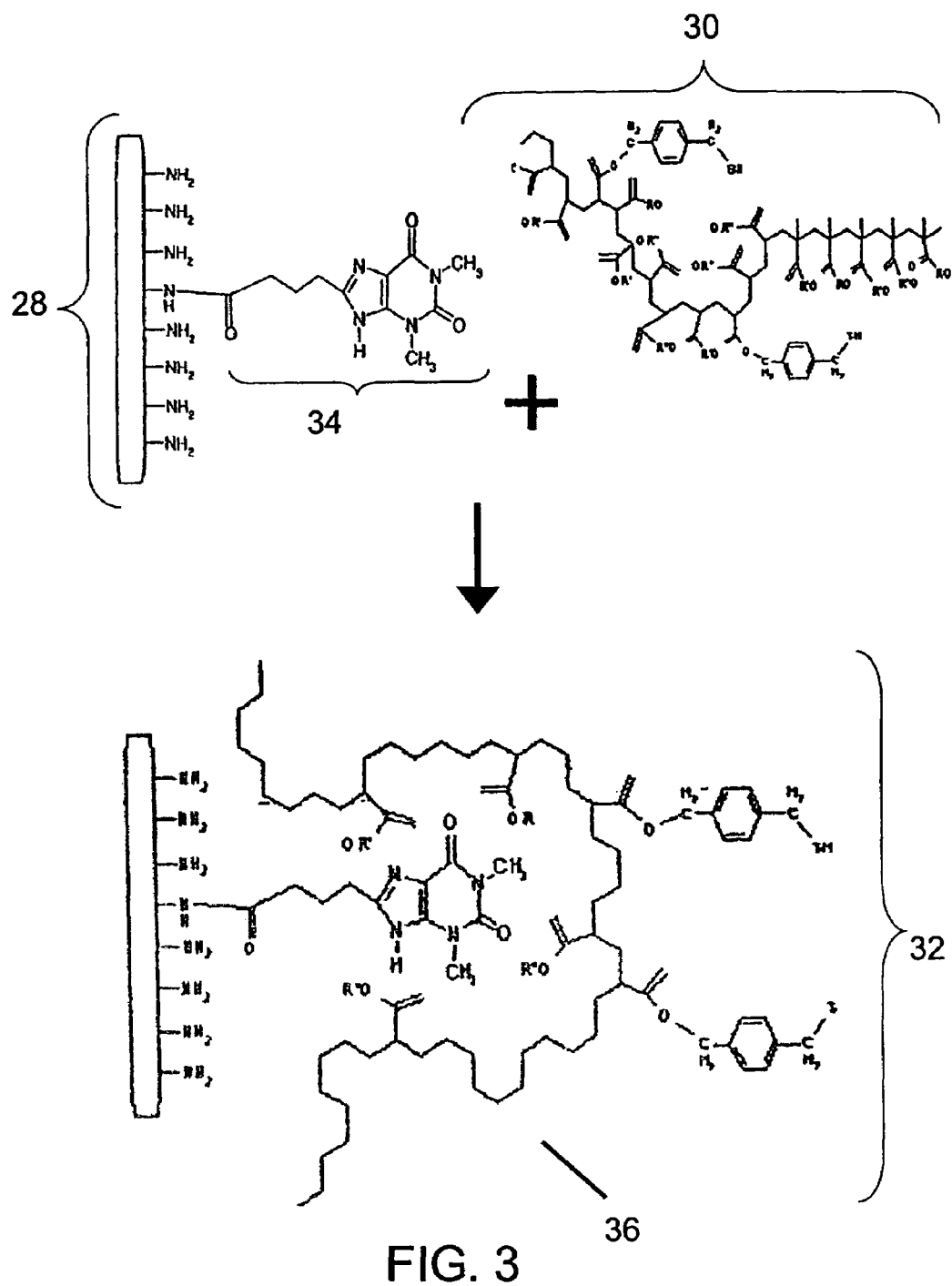
FIG. 3 illustrates the formation of binding cavity through the reaction of a guest molecule with a molecular target bound solid support and the formation of a solid support stamp.

FIG. 3 illustrates the formation of a binding cavity through the reaction of a guest molecule (polymer) with a molecular target-bound solid support forming a solid support stamp. A molecular target-bound solid support 28 is reacted with a thiol-derivatized polymer 30. The thiol-derivatized polymer forms a binding cavity 36 around the bound molecular target 34 through non-covalent interactions. Stearic restrictions form the binding cavity 36 into a defined conformation. This forms a solid support stamp 32.

By way of example, poly(methacrylic acid) is chosen as the primary building block for the introduction of multiple chemical functionalities. Prepolymer is converted to polymer with minor modification to literature procedure. Physical characterization based on $^1$H-NMR (singlet —OCH$_2$ at 4.85 ppm, broad aromatic protons in the range of 7.37-8.34 ppm) as well as the vinyl protons at 5.25, 5.76 and 6.70 ppm) characteristic of the presence of vinylbenzyl moiety is observed. IR spectroscopy also reveals intense absorptions at 1731 cm$^{-1}$, 1685 cm$^{-1}$ and 963 cm$^{-1}$ respectively, which are attributed to the presence of ester functionality, carboxylic acid functionality and vinyl functionality in the polymer chain in addition to characteristic methyl and methylene absorptions of the parent polymer.

In another example, novel thiol-containing methacrylate monomers are synthesized and characterized. The monomer is obtained in 61% yield as yellow viscous oil from the reaction of 2-hydroxyethylmethacrylate and 6-acetylthiohexanoic acid mediated by dicyclohexylcarbodiimide (DCC) and dimethylaminopyridine (DMAP) in dichloromethane for 72 hours at room temperature. After column chromatography, the monomer is obtained in reagent grade state and stored at 4° C. $^1$H-NMR and FT-IR analyses of the product prove the chemical structure of the desired monomer.

Using derivatized polymers as the guest molecule, poly (methacrylates) with carboxylic acid functional groups and with surface-attachable thiols are synthesized and characterized. These functional polymers due to their balanced hydrophobic hydrophilic behavior demonstrate good solution properties. The polymer is obtained in equimolar quantity (feed monomer ration 50:50) from monomeric precursors in AIBN at 70° C. for 24 h and is precipitated from dioxane to cold heptane resulting in a white powder, which is filtered off and vacuum dried. Polymers are obtained in (50:50 and 70:30) monomer feed ratio, respectively. A homopolymer is also synthesized for further comparison. All polymers are then deprotected via a milder procedure by refluxing them with a solution of 2N K$_2$CO$_3$ aqueous solution in methanol for 4 h followed by addition of 10 mL of 2N HCl and precipitated by heptane and vacuum dried. Polymers are characterized by differential scanning calorimetry (DSC), FT-IR, and thermogravimetric analysis (TGA) and gel permeation chromatography (GPC). Infrared spectroscopy of all polymeric samples reveals the presence of intense absorptions at 3400 cm$^{-1}$ which is attributed to the presence of carboxylic acid functionality in addition to the characteristic methyl, methylene and aromatic absorptions of the polymers.

Interaction of the theophylline-modified surface with a methacrylic add monomer is tested by covering the surface with the monomer for 5 minutes. The surface is rinsed thoroughly with hexane. XPS does not exhibit signals characteristic of methacrylic acid. ATR-FTIR spectrum of this surface presents new peaks.

After this step, polymerization of the methacrylic acid monomer is performed in the presence of the divinylbenzene (cross-linker) and AIBN (radical initiator) on top of the theophylline-modified surface. The ATR-IR spectrum after the polymerization exhibits the characteristic signature of the amide group (1660 and 1550 cm$^{-1}$). The peak at 1710 cm$^{-1}$ is shifted to 1705 cm$^{-1}$ corresponding to the carbonyl groups in the carboxylic acid of the polymer. These data prove that the attachment of the polymethacrylic acid is taking place. New peaks occur at 3094, 1634, 1596, 1511 and 1377 cm$^{-1}$. A spectrum of commercial polymethacrylic acid is taken in order to check if these peaks in fact correspond with the polymer.

To further test theophylline-methacrylic acid interaction, hydrophobic and hydrophilic PDMS (PDMS and PDMS after treatment with O$_2$ plasma) are covered with methacrylic acid for 5 minutes and rinsed with hexane and ethanol. ATR-FTIR spectra are taken for these samples before and after the methacrylic acid step. Peaks belonging to methacrylic acid at 1701, 1640, 1455, 1433, 1379, 950 cm$^{-1}$ were observed on both samples, indicating that methacrylic acid attaches to PDMS surfaces.

In another example, PDMS_vinylsilane is used in polymerization: the double bonds from the silane polymerize in the presence of the methacrylic acid, the initiator and the cross-linker thus covalently linking the polymer.

The first step involves the reaction of a vinylsilane with PDMS. Two different concentrations of the triethoxyvinylsilane (0.1M and 1M in ethanol) are used for the overnight reaction with PDMS_OH. ATR-FTIR spectra exhibit new peaks at 1600 cm$^{-1}$ (more intense for the 1M solution) and 1056 cm$^{-1}$. The 1600 cm$^{-1}$ region is characteristic of the C=C bond. XPS spectra also present stronger Si—C for the sample from 1M solution, confirming that the attachment takes place on the PDMS_OH substrates.

Figure 4:
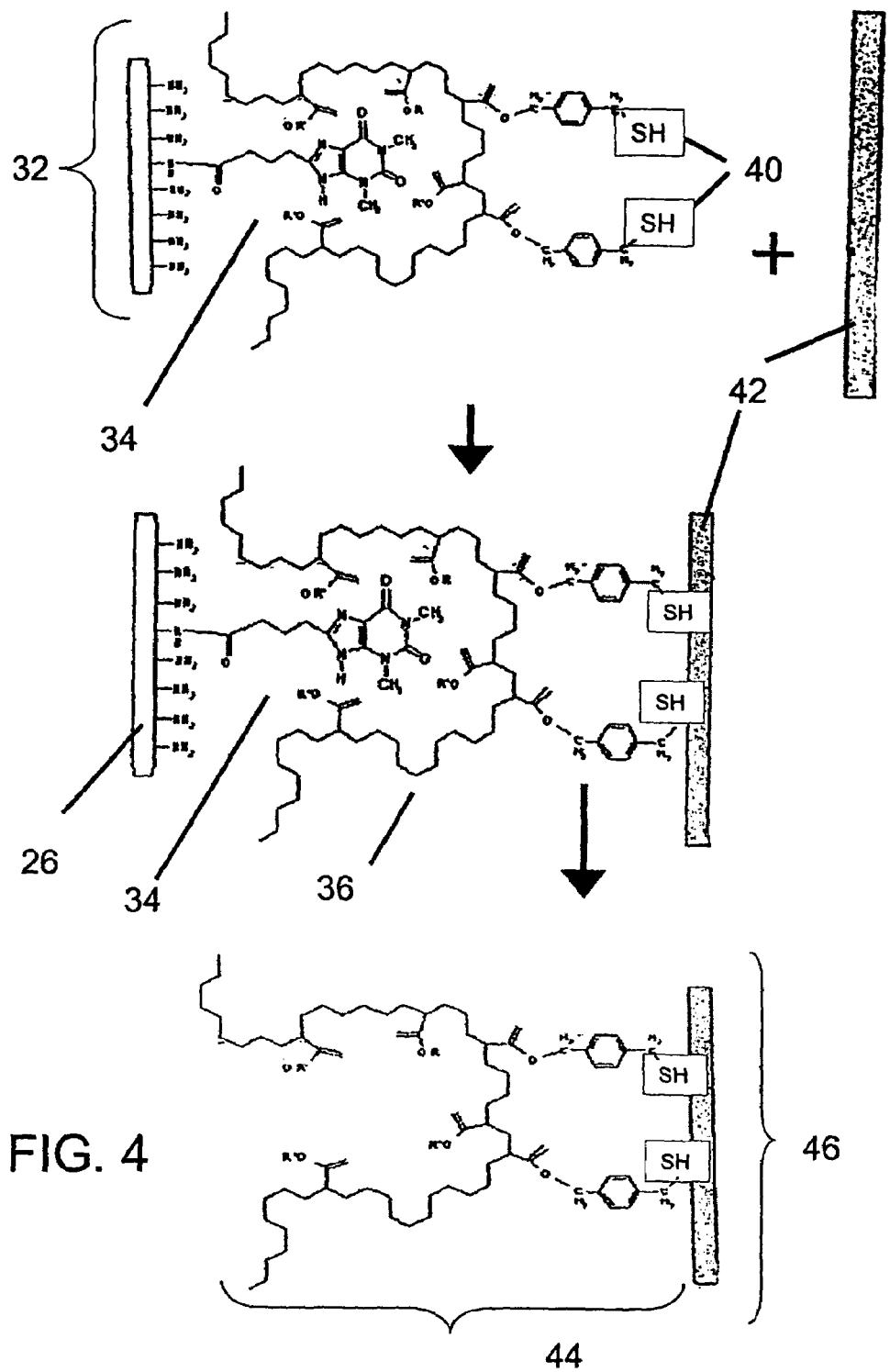
FIG. 4 illustrates the production of an embodiment of a molecularly-imprinted chemical detection device through the application of a solid support stamp to a solid substrate and the production a molecularly-imprinted polymer on the surface of the solid substrate.

FIG. 4 illustrates the production of a molecularly-imprinted chemical detection device through the application of a solid support stamp to a solid substrate and the production a molecularly-imprinted polymer on the surface of the solid substrate. A solid support stamp 32 is applied to a solid substrate 42 and is attached via thiol groups 40 on the solid support stamp. Both covalent and non-covalent (eg., electrostatic, acid-base, etc.) attachments of the binding cavity 36 to the solid substrate can be made. After removal of the solid support 26 and the bound molecular target 34, a molecularly-imprinted chemical detection device 46 with a molecularly-imprinted polymer 44 attached to it is produced.

Figure 5:
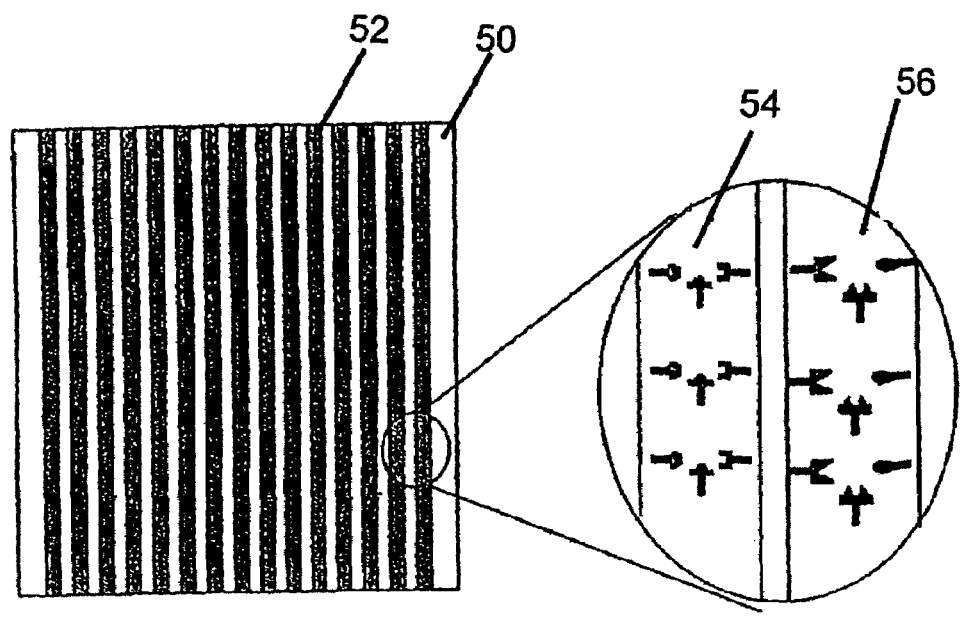
FIG. 5 illustrates one embodiment of a molecularly-imprinted chemical detection device with arrays of different molecularly-imprinted polymers on the surface of the solid substrate.

FIG. 5 illustrates one embodiment of a molecularly-imprinted chemical detection device with different molecularly-imprinted polymers on the surface of the solid substrate. An arrayed molecularly-imprinted chemical detection device 50 comprises several linear arrangements 52 of different molecularly-imprinted polymers. The device in this embodiment is developed from high resolution chemical patterning resulting in the fabrication of arrays of chemically and spatially-resolved functional groups onto defined substrate surfaces. In this embodiment, the arrayed molecularly-imprinted chemical detection device 50 is capable of detecting at least two different chemical targets using, for example, MIPs 54 and 56. The distance between the patterned linear arrangements 52 can be varied depending on the analytical detection method used. Using a distance of 10 µm, evanescent-based measurements can be taken, corresponding to the width of the waveguide, whereas a width of 1 µm can be used for SPR measurements, to as low as 50 nm for cantilever-based techniques.

In one embodiment of the present invention, a molecularly-imprinted chemical detection device is provided for use in the field, outside of the traditional laboratory setting. The device of the present invention can be used in numerous applications, e.g., environmental, military, or medical settings, for direct detection of chemical targets. Because the device can include an array of MIPs patterned on the surface of the solid substrate, a panel of chemical targets can be directly detected in situ. Detecting chemicals using this device involves exposing the device to that which is to be monitored and allowing the device to detect and quantify the binding of the chemical target to at least one MIP imprinted on the surface of the device. Detection and quantification using one or more analytical detection methods (such as evanescent-based, SPR, cantilever-based techniques, etc.) in the device of the present invention can be done immediately at the area of exposure.

In summary, embodiments of the invention described herein represent improvements over prior art molecularly-imprinted chemical devices. The invention described in the present invention provides a more convenient method of producing a molecularly-imprinted chemical detection device. The invention provides a high-throughput, highly-reliable molecular imprinting method while reducing costs, saving considerable time and eliminating the use of harsh chemical degradation. Further, the invention provides a portable molecularly-imprinted chemical detection device for the detection and quantification of bound chemical targets in situ outside of the laboratory setting using commonly-available and more feasible analytical techniques.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A method of producing a molecularly-imprinted chemical detection device comprising the steps of:
    a) modifying the surface of a solid support through the attachment of functional groups;
    b) reacting the solid support with a derivatized molecular target to form a molecular target bound solid support;
    c) reacting the molecular target bound solid support with at least one guest molecule thus forming a solid support stamp having a binding cavity around the molecular target, the binding cavity having one or more functional groups which allow attachment of the binding cavity to a solid substrate;
    d) selecting the solid substrate for facilitating attachment of the binding cavity on the solid support stamp to the solid substrate;
    e) applying the solid support stamp to a surface of the solid substrate to attach the binding cavity to the solid substrate; and
    f) removing the molecular target with the solid support to produce a molecularly-imprinted polymer on the surface of the solid substrate.

2. The method of claim 1 wherein the at least one guest molecule is at least one derivatized functional monomer forming at least one functional monomer recognition element around the molecular target.

3. The method of claim 2 wherein at least two functional monomer recognition elements are polymerized the form the binding cavity around the molecular target.

4. The method of claim 1 wherein the guest molecule is at least one derivatized functional polymer.

5. The method of claim 1 wherein a silicon wafer solid support is modified to facilitate the attachment in step (a).

6. The method of claim 1 wherein the surface of the solid support is modified with amino-siloxane.

7. The method of claim 1 wherein the solid substrate is a coated slide.

8. The method of claim 7 wherein the coated slide is a coated glass slide.

9. The method of claim 7 wherein the coated slide is coated with one of gold and silicon dioxide.

10. The method of claim 1 wherein a plurality of binding cavities are attached to the solid substrate producing a plurality of molecularly-imprinted polymers.

11. The method of claim 10 wherein at least two different binding cavities are attached to the solid substrate producing at least two different molecularly-imprinted polymers segregated into separate areas.

12. The method of claim 1 wherein the solid support stamp is applied to a surface of a solid substrate having an area of about 1 to 2 cm$^2$.

13. A method of producing a molecularly-imprinted chemical detection device using a solid support stamp produced from a molecular target bound solid support, having a binding cavity around the molecular target, the binding cavity having one or more functional groups which allow attachment of the binding cavity to a solid substrate, comprising the steps of:
    a) selecting the solid substrate for facilitating attachment of the binding cavity on the solid support stamp to the solid substrate;
    b) applying the solid support stamp to the surface of the solid substrate to attach the binding cavity to the solid substrate; and
    c) removing the molecular target bound solid support to produce a molecularly-imprinted polymer on the surface of the solid substrate.

14. The method of claim 13 wherein the solid support stamp is applied to a surface of a coated slide in step (b).

15. The method of claim 14 wherein the coated slide is a coated glass slide.

16. The method of claim 14 wherein the coated slide is coated in one of gold and silicon dioxide.

17. The method of claim 13 wherein a plurality of binding cavities are attached to the solid substrate producing a plurality of molecularly-imprinted polymers.

18. The method of claim 13 wherein at least two different binding cavities are attached to the solid substrate producing at least two different molecularly-imprinted polymers segregated into separate areas.

* * * * *